United States Patent
Sugai et al.

(10) Patent No.: US 7,230,110 B2
(45) Date of Patent: Jun. 12, 2007

(54) PYRITHIONE COMPOUND AND MICROCAPSULE USING THE SAME

(75) Inventors: Masaharu Sugai, Haibara-gun (JP); Koki Nakamura, Fujinomiya (JP); Yoshihiro Jimbo, Minami-ashigara (JP); Mitsuyuki Tsurumi, Fujinomiya (JP)

(73) Assignee: FujiFilm Corporation, Tokyo (JP)

( * ) Notice: Subject to any disclaimer, the term of this patent is extended or adjusted under 35 U.S.C. 154(b) by 0 days.

(21) Appl. No.: 11/139,617

(22) Filed: May 31, 2005

(65) Prior Publication Data
US 2005/0271736 A1    Dec. 8, 2005

(30) Foreign Application Priority Data
Jun. 2, 2004    (JP) ............................. 2004-165060

(51) Int. Cl.
*C07D 211/84*    (2006.01)
(52) U.S. Cl. ................................... 546/296
(58) Field of Classification Search .............. 546/296
See application file for complete search history.

(56) References Cited

FOREIGN PATENT DOCUMENTS

| JP | 2000-296675 A | 10/2000 |
|---|---|---|
| JP | 2004-43421 A | 2/2004 |

OTHER PUBLICATIONS

Abu-Dari et al, Inorganic Chemistry, vol. 3, No. 3, pp. 519-524, 1991.*

Jens Hartung et al., J. Org. Chem, 1995, 60, pp. 6706-6716.
Doug Burdi et al., Journal of the American Chemical Society, vol. 119, No. 28 Jul. 16, 1997, pp. 6457-6460.

* cited by examiner

*Primary Examiner*—Zinna N. Davis
(74) *Attorney, Agent, or Firm*—Birch, Stewart, Kolasch & Birch, LLP

(57) ABSTRACT

A compound represented by formula (I); a multifunctional isocyanate composition, containing an adduct formed by treating the compound represented by formula (I) with a compound represented by formula (II); and a microcapsule using the multifunctional isocyanate composition:

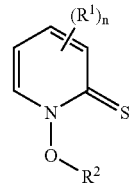

Formula (I)

wherein, in formula (I), $R^1$ represents $-L^1-X^1$ or $X^1$; $R^2$ represents a hydrogen atom or $-L^2-X^2$; $L^1$ and $L^2$ each independently represent a divalent linking group; $X^1$ and $X^2$ each independently represent a nucleophilic substituent; n represents an integer of 1 to 4; and when n is 2 or more, $R^1$s may be the same or different; and $$R^3-(NCO)_m$$   Formula (II)

wherein, in formula (II), $R^3$ represents an arbitrary m-valent linking group; and m represents an integer of 2 or above.

4 Claims, No Drawings

PYRITHIONE COMPOUND AND MICROCAPSULE USING THE SAME

FIELD OF THE INVENTION

The present invention relates to a pyrithione compound (2-mercaptopyridine-N-oxide skeleton) having a property of decomposing upon exposure to light. The invention also relates to an adduct formed by treating the pyrithione compound with a polyvalent isocyanate compound, and it further relates to a microcapsule comprising, as capsule walls, a polymer obtained by polymerization of such an adduct.

BACKGROUND OF THE INVENTION

Pyrithione compounds are typical compounds used in anti-Malassezia-furfur agents, anti-fouling agents for fishing nets, or antiseptics. However, pyrithione (2-mercaptopyridine-N-oxide) is a highly irritating compound, and further, it is not stable chemically, and gradually converts into a disulfide body. Therefore, there are few actual cases in which pyrithion itself is used in industrial bactericides. For instance, pyrithione antimicrobial agents are generally known as sodium pyrithione, zinc pyrithione, and copper pyrithione. These metal pyrithiones exhibit very high antimicrobial activities, but they have respective drawbacks. Sodium pyrithione, for example, is unstable in a dried state, and it is difficult to handle. Zinc pyrithione and copper pyrithione are poor in solvent solubility, such that even mixtures of them with other industrial bactericides were unsuccessful in attempts to enhance antimicrobial power. In addition, all these pyrithione compounds have a simple structure with no substituents on their respective rings.

As an example of antiseptics intended to resolve the foregoing problems, chlorohexidin-2-mercaptopyridine-N-oxide is disclosed in JP-A-2004-43421 ("JP-A" means unexamined published Japanese patent application). Although this agent obtained by combining chlorohexidin as a bactericidal disinfectant with 2-mercaptopyridine-N-oxide is improved in bactericidal strength, it still has the simple structure with no substituent on the pyrithione ring.

There are very few pyrithione compounds known to have a substituent on their respective rings. One example of such a compound is described in the *Journal of Organic Chemistry*, 1995, p. 6706.

In addition, an amino acid moiety-introduced pyrithione derivative is described in the *Journal of the American Chemical Society*, 1997, p. 6457. Therein, it is stated that the N—O bond is severed in a quantum yield of about 1.0, to produce radicals, when the derivative is irradiated with light of wavelengths in the visible to near ultraviolet region.

Pyrithione compounds, having such a photo-decomposing property, have potential as photo-functional materials. To develop such materials, it is necessary to introduce various substituents into the foregoing simple structure, which can lead to various derivatives, and to impart thereto not only the photo-decomposing property but also a variety of desired properties. To create photo-functional materials in particular, it is necessary to obtain pyrithione derivatives having various substituents. Further, introduction of reactive sections enabling reaction with other compounds, in addition to mere substituents, becomes important for obtaining novel pyrithione derivatives.

On the other hand, microcapsules capable of changing their permeability to some substances by various stimuli have been studied. For instance, microcapsules for encapsulating functional materials, such as medicines, agricultural chemicals, insect repellents, or perfumes, have been offered. As medicine-encapsulated microcapsules, drug delivery systems have been proposed. And slow-release agricultural chemicals have been proposed as agricultural chemical-encapsulated microcapsules. In addition, microcapsules making the most of thermal changes in their permeability to certain substances have been studied for heat-sensitive recording materials. In such microcapsules, color-forming materials (e.g. diazonium salts or leuco dyes) are encapsulated. Alternatively, microcapsules making the most of changes caused in their permeability to certain substances by application of pressure thereto have also been studied, for pressure-sensitive recording materials. In such microcapsules also, color-forming materials (e.g. diazonium salts or leuco dyes) are encapsulated. As microcapsules changing their permeability to certain substances by exposure to light, microcapsules for light- and heat-sensitive recording materials have been proposed. For instance, a description of such microcapsules can be found in JP-A-2000-296675.

SUMMARY OF THE INVENTION

The present invention resides in a compound represented by formula (I):

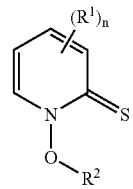

Formula (I)

wherein, in formula (I), $R^1$ represents -$L^1$-$X^1$ or $X^1$; $R^2$ represents a hydrogen atom or -$L^2$-$X^2$; $L^1$ and $L^2$ each independently represent a divalent linking group; $X^1$ and $X^2$ each independently represent a group selected from the group consisting a hydroxyl group, an amino group and a mercapto group; n represents an integer of 1 to 4; and when n is 2 or more, $R^1$s may be the same or different.

Further, the present invention resides in a multifunctional isocyanate composition, comprising an adduct formed by treating the compound represented by formula (I) described above with a compound represented by formula (II):

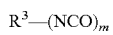

Formula (II)

wherein, in formula (II), $R^3$ represents an arbitrary m-valent linking group; and m represents an integer of 2 or above.

Further, the present invention resides in a microcapsule using the above-described multifunctional isocyanate composition.

Other and further features and advantages of the invention will appear more fully from the following description.

DETAILED DESCRIPTION OF THE INVENTION

According to the present invention, there is provided the following means:

(1) A compound represented by formula (I):

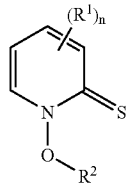

Formula (I)

wherein, in formula (I), $R^1$ represents $-L^1-X^1$ or $X^1$; $R^2$ represents a hydrogen atom or $-L^2-X^2$; $L^1$ and $L^2$ each independently represent a divalent linking group; $X^1$ and $X^2$ each independently represent a group selected from the group consisting a hydroxyl group, an amino group and a mercapto group; n represents an integer of 1 to 4; and when n is 2 or more, $R^1$s may be the same or different.

(2) The compound according to the above item (1), wherein, in formula (I), n is 1.

(3) A multifunctional isocyanate composition, comprising an adduct formed by treating the compound represented by formula (I) according to the above item (1) with a compound represented by formula (II):

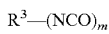

$R^3-(NCO)_m$     Formula (II)

wherein, in formula (II), $R^3$ represents an arbitrary m-valent linking group; and m represents an integer of 2 or above.

(4) The multifunctional isocyanate composition according to the above item (3), wherein the compound represented by formula (II) is 2,4-tolylene diisocyanate, 2,6-tolylene diisocyanate, m-xylylene diisocyanate, 1,6-hexamethylene diisocyanate, 2,5-di(isocyanatomethyl)norbornane, 4,4'-diphenylmethane diisocyanate, hydrogenated m-xylylene diisocyanate, hydrogenated 4,4'-diphenylmethane diisocyanate, or a mixture thereof.

(5) A microcapsule for encapsulating an organic or inorganic compound, wherein capsule walls of the microcapsule comprises at least a polymer of the multifunctional isocyanate composition according to the above item (3) or (4).

Our intensive studies have revealed that a pyrithione derivative having a reactive (nucleophilic) site can be obtained; and, the use of the pyrithione compound makes it possible to provide a photo-responsive microcapsule. The present invention has been realized based on these findings.

In the present invention, the term "photo-decomposability (photo-disintegrating property)" means that the bond formed between the nitrogen atom in the pyrithione nucleus (ring) and the oxygen atom attached thereto is cleaved by light.

The present invention is described below in detail.

At first, the compound (pyrithione compound) represented by formula (I) according to the present invention is described below.

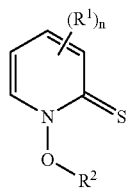

Formula (I)

In formula (I), $R^1$ represents $-L^1-X^1$ or $X^1$, and $R^2$ represents a hydrogen atom or $-L^2-X^2$. $L^1$ and $L^2$ each independently represent a divalent linking group, and $X^1$ and $X^2$ each independently represent a nucleophilic substituent selected from a hydroxyl group, an amino group or a mercapto group. n represents an integer of 1 to 4, and when n is 2 or more, $R^1$s may be the same or different.

It is preferable that $X^1$ and $X^2$ each are a hydroxyl group. And, n is preferably 1.

$L^1$ and $L^2$ each independently represent a divalent linking group by which the pyrithione ring is connected to $X^1$ or $X^2$. Examples thereof include an alkylene group, an alkenylene group, an alkynylene group, an arylene group, —O—, —S—, —NR—, —CO—, —COO—, —NRCO—, —SO$_2$—, and combinations of two or more of these divalent groups. Herein, R represents a hydrogen atom or a substituent. When $L^1$ or $L^2$ is the combination of an alkylene group and —NR—, R may bond to the alkylene group to form a ring.

Examples of the substituent represented by R include an alkyl group (e.g. a methyl group and an ethyl group), an aralkyl group (e.g. a phenylmethyl group), an alkenyl group (e.g. an allyl group), an alkynyl group, a hydroxyalkyl group (e.g. a hydroxyethyl group), an aryl group (e.g. a phenyl group and a p-methoxyphenyl group), a carbonyl group, an acyl group (e.g. an acetyl group and a benzoyl group), an alkoxycarbonyl group (e.g. a methoxycarbonyl group), and an acyloxy group (e.g. an acetoxy group). Of these substituents, an alkyl group and a hydroxyalkyl group are preferred over the others. When those substituents have carbon atoms, the number of the carbon atoms is preferably from 1 to 20, and more preferably from 1 to 10.

The more detailed description of $L^1$ and $L^2$ is as follows. The alkylene group represented by $L^1$ or $L^2$ may be a straight-chain, branched or cyclic alkylene group, and it is preferably an alkylene group having 1 to 20 carbon atoms, more preferably an alkylene group having 2 to 10 carbon atoms. Examples thereof include a methylene group, an ethylene group, a trimethylene group, a propylene group, a butylene group, a hexylene group and a cyclohexylene group. The alkylene group as mentioned above may further have a substituent. Examples of the substituent which the alkylene group may have include an alkyl group (e.g. a methyl group, an ethyl group), an aralkyl group (e.g. a phenylmethyl group), an alkenyl group (e.g. an allyl group), an alkynyl group, an alkoxy group (e.g. a methoxy group, an ethoxy group), a hydroxyalkyl group (e.g. a hydroxyethyl group), an aryl group (e.g. a phenyl group, a p-methylphenyl group), an amino group (e.g. a unsubstituted amino group, a dimethylamino group), an acylamino group (e.g. an acetylamino group), a sulfonylamino group (e.g. a methanesulfonylamino group), a ureido group, a urethane group, an aryloxy group (e.g. a phenyloxy group), a sulfamoyl group (e.g. a methylsulfamoyl group), a carbamoyl group (e.g. a unsubstituted carbamoyl group, a methylcarbamoyl group), an alkylthio group (e.g. a methylthio group), an arylthio group (e.g. a phenylthio group), a sufonyl group (e.g. a methanesulfonyl group), a sulfinyl group (e.g. a methanesulfinyl group), a hydroxy group, a halogen atom (e.g. a chlorine atom, a bromine atom, a fluorine atom), a cyano group, a sulfo group, a carbonyl group, a phosphono group, an aryloxycarbonyl group (e.g. a phenyloxycarbonyl group), an acyl group (e.g. an acetyl group, a benzoyl group), an alkoxycarbonyl group (e.g. a methoxycarbonyl group), an acyloxy group (e.g. an acetoxy group), a carbonamido group, a sulfonamido group, a nitro group, a hydroxamic acid group, and a heterocyclic group. Of these substituents, an alkyl group, a hydroxy group and a hydroxyalkyl group are preferred over the others. When the substituents recited above have carbon atoms, the number of the carbon atoms is preferably from 1 to 30, more preferably from 1 to 10.

The alkenylene group and the alkynylene group may be in straight-chain, branched or cyclic form, and those each contain preferably 2 to 10 carbon atoms. These alkenylene and alkynylene groups each may further have a substituent. Examples and the preferable range of the substituent are the same as those regarding the alkylene group.

The arylene group is preferably a monocyclic or condensed cyclic arylene group having 6 to 30 carbon atoms, more preferably a monocyclic or condensed cyclic arylene group having 6 to 20 carbon atoms. Examples thereof include a phenylene group and a naphtylene group. The phenylene group is particularly preferable. Such an arylene group may further have a substituent. Examples and the preferable range of such a substituent are the same as those regarding the alkylene group. The substituent may further be substituted with themselves.

$L^1$ is more preferably an alkylene group, an arylene group, —O—, —S—, —NR—, —COO—, —NRCO— (in which R is a hydrogen atom or a substituent), a combination of any two or more of groups recited above, or a combination of an alkylene group and —NR— whose R bonds to the alkylene group to form a ring. Of these groups, the combination of an alkylene group with —O—, —NRCO— or —COO—, especially —O-alkylene-(in which the alkylene is attached to the pyrithione ring via the oxygen atom), is preferred over the others.

$L^2$ is more preferably an alkylene group, an arylene group, —COO—, —CONR— (in which R is a hydrogen atom or a substituent), or a combination of any two or more of the groups recited above. Of these groups, the combination of an alkylene or arylene group with —CONR— or —COO— is preferred over the others.

Preferred examples of $R^1$ are 6-hydroxyhexyloxy group (—O—(CH$_2$)$_6$—OH) and 4-hydroxybutyloxy (—O—(CH$_2$)$_4$—OH) group, and those of $R^2$ are 6-hydroxyhexyl group and 4-hydroxybutyl group. Further, it preferable that $R^1$ is attached to the 3-position of the pyrithione ring. In the introducing method of $R^1$ and $R^2$ into the pyrithione ring, it is preferable that $R^1$ be introduced first, and then $R^2$ be introduced. More specifically, it is preferable to use, as a starting material, a pyridine compound that has, on the carbon atom adjacent to the nitrogen atom (on the 2-position), a substituent capable of being replaced by another substituent later on, such as a halogen atom, and that has, on the other carbon atom (e.g. on the 3-, 4- or 5-position, preferably on the 3-position), a substituent (e.g. as a hydroxyl group and a carboxyl group).

Introduction of $R^1$ into such a starting material is described below. When a starting material having, for example, a hydroxyl group at the 3-, 4- or 5-position is used, the hydroxyl group can be modified by reaction with an electrophilic agent, such as a tosylate or halogen compound, in the presence of a base (such as potassium carbonate or sodium carbonate). When a starting material substituted by a carboxyl group at the 3-, 4- or 5-position is used, $R^1$ can be introduced by converting the carboxyl group into acid chloride and then allowing the acid chloride to react with an appropriate nucleophilic acid (such as a compound having an amino or hydroxyl group). The foregoing electrophilic or nucleophilic agent may contain a linking group (corresponding to $L^1$), such as an alkylene group or —O—, in its molecule, and it is preferable that the agent has a nucleophilic moiety (corresponding to $X^1$), such as a hydroxyl group, in its molecule. Such a nucleophilic moiety is preferably protected with an appropriate protective group. Examples of the protective group include a pivaloyl group, an acetyl group and a 1-butyldimethylsilyl group.

Introduction of $R^2$ is carried out after the pyridine derivative prepared in the aforementioned manner is converted into the pyrithione skeleton. The conversion into the pyrithione skeleton can be performed by deriving a pyridine oxide from the above-described pyridine derivative under the action of an appropriate oxidant (e.g. 3-chloroperbenzoic acid and hydrogen peroxide), and then by allowing sodium hydrosulfide to act thereon. The $R^2$'s introduction subsequent thereto can be performed by reaction with an electrophilic agent, such as a tosylate and halogen compound, in the presence of a base (e.g., potassium carbonate and sodium carbonate). The electrophilic agent as mentioned above may contain a linking group (corresponding to $L^2$), such as an alkylene group or —O—, in its molecule, and it is preferable that the agent has a nucleophilic moiety (corresponding to $X^2$), such as a hydroxyl group, in its molecule. Such a nucleophilic moiety is preferably protected with an appropriate protective group. Examples of the protective group include a pivaloyl group, an acetyl group and a t-butyldimethylsilyl group.

When the thus prepared compound has a protective group introduced into the substituent corresponding to $X^1$ or $X^2$, the compound of the present invention can be derived from such a compound via a de-protection process.

Specific examples of the compound represented by formula (I) are illustrated below, but the present invention is not limited to those shown.

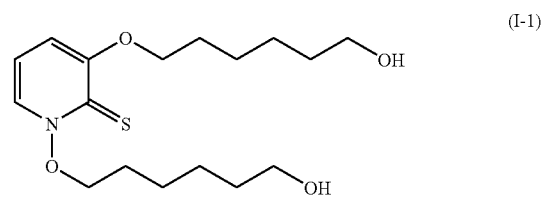

(I-1)

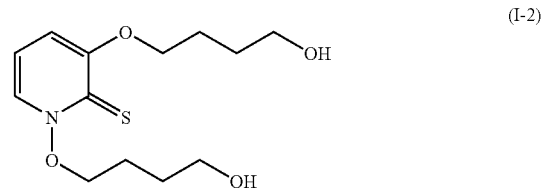

(I-2)

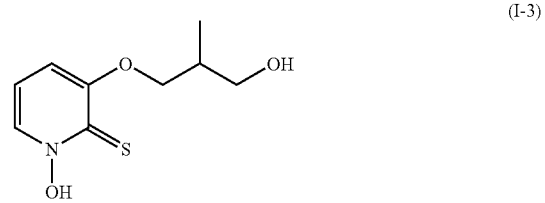

(I-3)

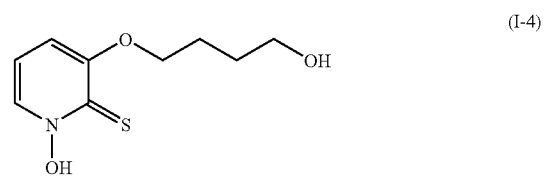

(I-4)

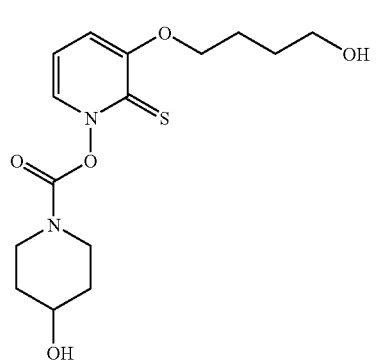 (I-5)
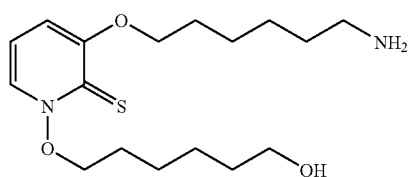 (I-6)
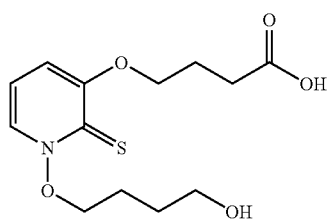 (I-7)
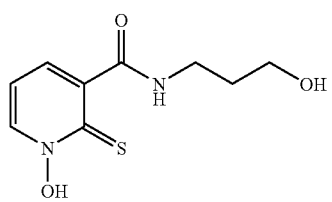 (I-8)
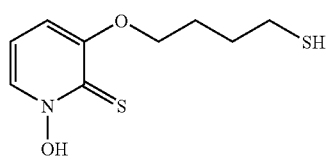 (I-9)
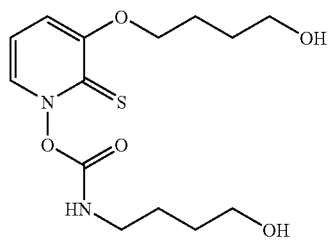 (I-10)
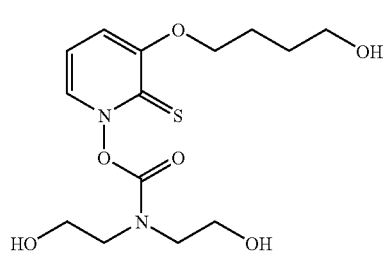 (I-11)
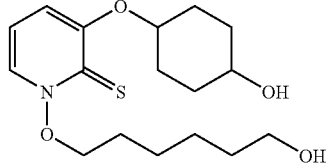 (I-12)
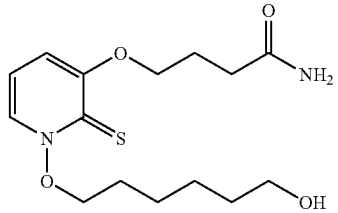 (I-13)
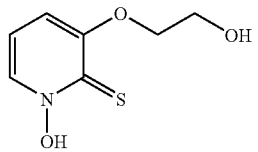 (I-14)
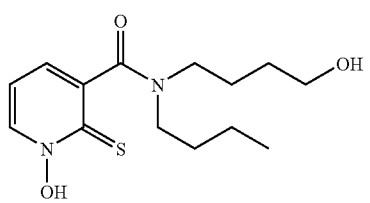 (I-15)
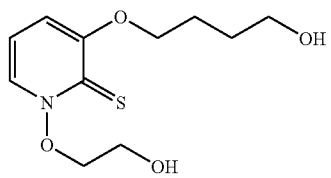 (I-16)
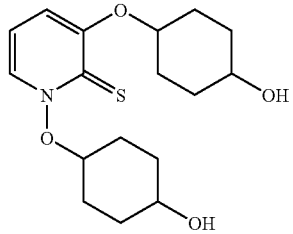 (I-17)
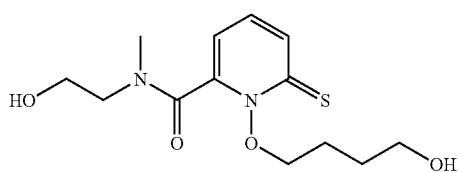 (I-18)

-continued (I-19)
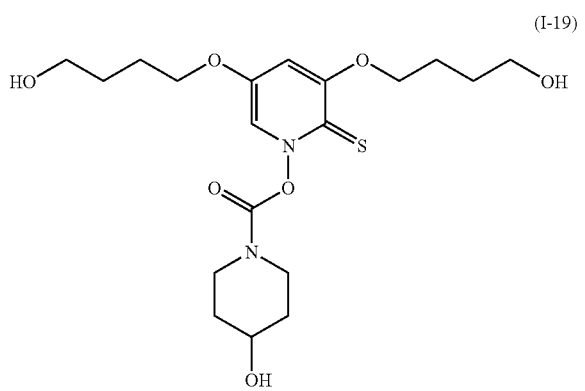

(I-20)
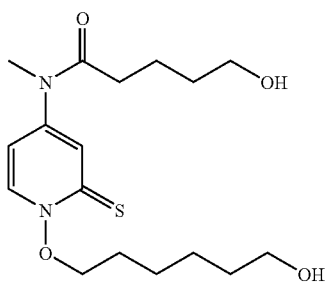

(I-21)
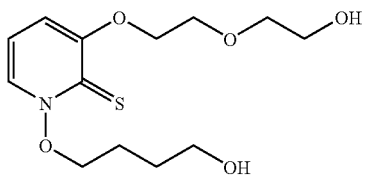

(I-22)
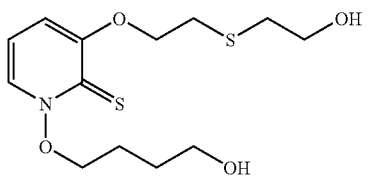

(I-23)
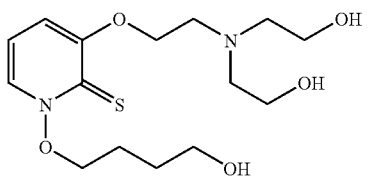

(I-24)
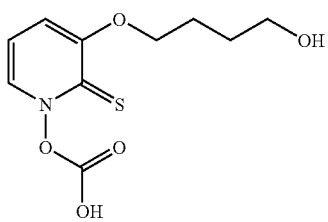

-continued (I-26)
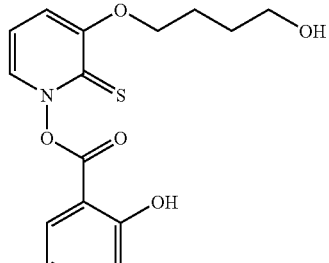

(I-27)
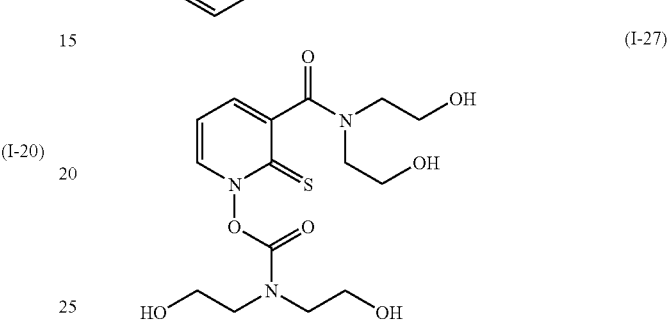

The multifunctional isocyanate composition that can be used in the present invention is described below. The multifunctional isocyanate composition that can be used in the present invention is a multifunctional isocyanate composition comprising an adduct formed by treating the above-described compound represented by formula (I) with a compound represented by formula (II).

$$R^3-(NCO)_m \qquad \text{Formula (II)}$$

In formula (II), $R^3$ represents an arbitrary m-valent linking group, and m represents an integer of 2 or above. As the compound represented by formula (II), any of arbitrary compounds can be used. Such compounds are difunctional, trictional and higher-order multifunctional isocyanate compounds. The compound represented by formula (II) has no particular restriction so far as the compound is a multifunctional isocyanate compound. In addition, $R^3$ has no particular restriction. m is preferably from 2 to 5, particularly preferably 2 or 3. The compound represented by formula (II) can be synthesized in accordance with an ordinary method. Examples of the compound represented by formula (II) include an aromatic isocyanate compound and an aliphatic isocyante compound.

Examples of the difunctional isocyanates represented by formula (II) include an aromatic difunctional isocyanate, such as 2,4-tolylene diisocyanate, 2,6-tolylene diisocyanate, m-phenylene diisocyanate, p-phenylene diisocyanate, m-xylylene diisocyanate, p-xylylene diisocyanate, 4-chloroxylylene-1,3-diisocyanate, 2-methylxylylene diisocyanate, 4,4'-diphenylmethane diisocyanate, 4, 4'-diphenylpropane diisocyanate, 4,4'-diphenylhexafluoropropane diisocyanate, 1,4-naphthalene diisocyanate, 3,3'-dimethoxybiphenyl diisocyanate and 3,3'-dimethyldiphenylmethane-4,4'-diisocyanate; an aliphatic difunctional isocyanate, such as 1,3-trimethylene diisocyanate, propylene-1,2-diisocyanate, butylene-1,2-diisocyanate, 1,6-hexamethylene diisocyanate, cyclohexylene-1,2-diisocyanate, cyclohexylene-1,3-diisocyanate, cyclohexylene-1,4-diisocyanate, isophorone diisocyanate, hydrogenated m-xylylene diisocyanate, hydrogenated p-xylylene diisocyanate, hydrogenated 4,4'-diphenylmethane diisocyanate and 2,5-di(isocyanatomethyl)norbornane; and an addition product of the difunctional isocyanates as recited above with a phenol or a difunctional alcohol, such as an ethylene glycol or a bisphenol.

Examples of the trifunctional or higher-order multifunctional isocyanate represented by formula (II) include a trimers prepared by using the above-described isocyanate as a main starting material (e.g., biuret and isocyanuric acid esters); an addition product derived mainly from the difunctional isocyanates as recited above with a trifunctional alcohol (e.g., trimethylolpropane) or a trifunctional phenol (e.g., phloroglucin); a formaldehyde condensate of a benzene isocyanate (e.g. polymethylenepolyphenylene polyisocyanate); a polymer of an isocyanate compound containing a polymerizing group (e.g., methacryloyloxyethyl isocyanate); and a lysine triisocyanate.

Particularly preferred examples of the compound represented by formula (II) include 2,4-tolylene diisocyanate, 2,6-tolylene diisocyanate, m-xylylene diisocyanate, 1,6-hexamethylene diisocyanate, 2, 5-di(isocyanatomethyl)norbornane, 4,4'-diphenylmethane diisocyanate, hydrogenated m-xylylene diisocyanate, hydrogenated 4,4'-diphenylmethane diisocyanate, and a mixture of two or more of the diisocyanates recited above.

The multifunctional isocyanate composition that can be used in the present invention can be prepared by nucleophilic addition reaction between the hydroxyl, amino or mercapto group in the compound represented by formula (I) and the isocyanate group in the compound represented by formula (II). In this connection, the molar ratio between the compound represented by formula (I) and the compound represented by formula (II) is preferably more than 1 but 10 or less, and more preferably 2 or more but 5 or less, expressed in terms of m/(n+1) (wherein m is the number of isocyanate groups in formula (II) and (n+1) is the total number of $X^1$ and $X^2$ in formula (I).

The multifunctional isocyanate composition of the present invention is made into a polymer by undergoing addition polymerization, and this polymer can be used as a material for microcapsule walls, to prepare a microcapsule. The microcapsule of the present invention can encapsulate an organic or inorganic compound, such as a color-forming material, and can be applied suitably to the fields of a photosensitive recording material encapsulating the color-forming material, a drug delivery system encapsulating a drug, and a slow-release agricultural chemical encapsulating an agricultural chemical.

The microcapsule of the present invention can be produced in accordance with an interfacial polymerization method. For instance, it can be produced by dissolving a material to be encapsulated in the microcapsule and the multifunctional isocyanate compound of the present invention into a hydrophobic solvent (an oil phase), adding the resulting oil phase to an aqueous solution of a water-soluble polymer (a water phase), and then emulsifying and dispersing the resultant mixture by means of a homogenizer or the like, and thereby forming a polymer film to make a microcapsule wall at the interface between the oil phase and the water phase. More specifically, the microcapsule can be produced using the methods described, for example, in U.S. Pat. Nos. 3,726,804 and 3,796,699, *Microcapsules* written by Tomoji Kondo and published by the Nikkan Kogyo Shimbun Ltd. in 1970, and *Microcapsules* written by Tamotsu Kondo et al. and published by Sankyo Shuppan Co., Ltd. in 1977.

According to the present invention, it is possible to provide a pyrithione derivative having a reactive site. Further, according to the present invention, it is possible to provide a microcapsule making the most of the photo-decomposability of the pyrithione.

The pyrithione compound of the present invention has photo-decomposability (photo-disintegrating property), and it further has a reactive (nucleophilic) site. Therefore, it is possible to use the pyrithione compound as a wall material of a microcapsule, and provide a photo-responsive material.

In addition, the microcapsule of the present invention changes its permeability to certain substances when exposed to light, and therefore it is useful as a microcapsule for a photosensitive recording material.

The present invention will be described in more detail based on examples given below, but the invention is not meant to be limited by these.

EXAMPLES

Example 1

<Synthesis of Exemplified Compound (I-1)>

The exemplified compound (I-1) was synthesized in accordance with the following scheme:

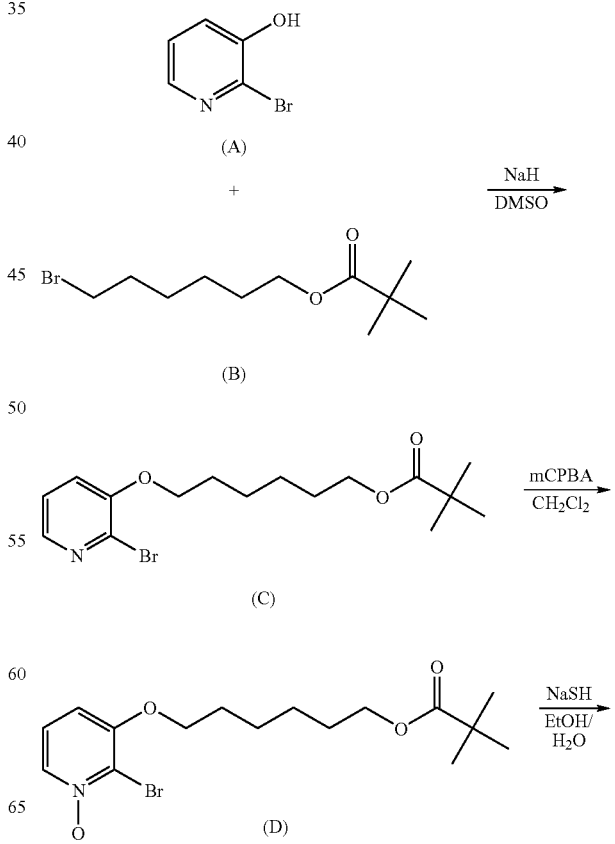

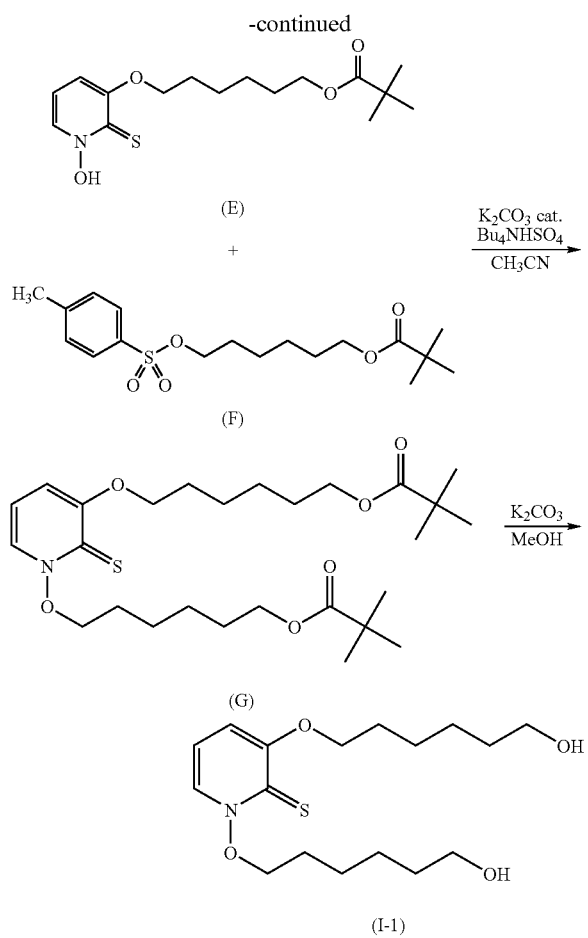

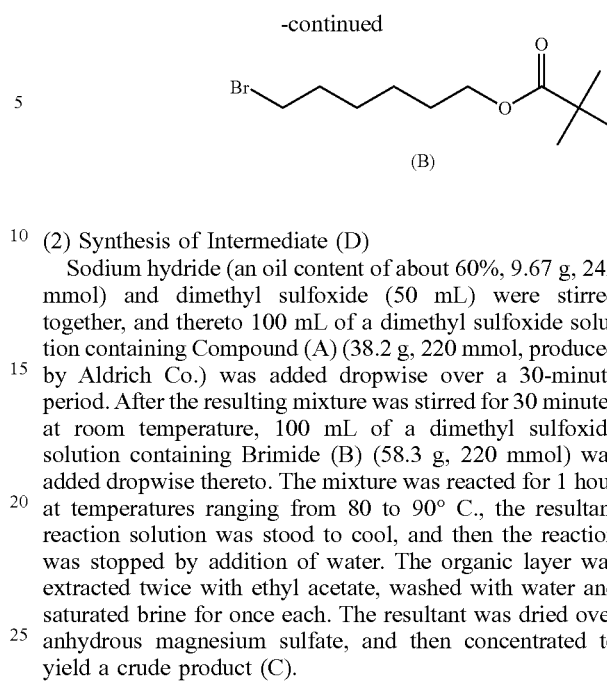

(1) Synthesis of Intermediate (B)

6-Bromo-1-hexanol (L) (99.2 g, 548 mmol, produced by Aldrich Co.) and methylene chloride (250 mL) were stirred together, and thereto pyridine (48.7 mL, 603 mmol) was added. Further, pivaloyl chloride (70.9 mL, 575 mmol) was added dropwise thereto while ice cooling, and then the resulting mixture was stirred for 5 hours at room temperature. The reaction solution obtained was washed with diluted hydrochloric acid and saturated brine for once each. The washed solution was dried over anhydrous magnesium sulfate and then concentrated to yield a crude product. The crude product obtained was purified by silica gel column chromatography (eluate: 9:1 mixture of hexane with ethyl acetate) to give 134 g of Intermediate (B) as an oily matter (in a 92% yield).

NMR Spectrum of Intermediate (B)

$^1$H-NMR (CDCl$_3$): δ 1.20 (s, 9H), 1.30–1.50 (m, 4H), 1.65 (m, 2H), 1.88 (m, 2H), 3.41 (t, 2H), 4.07 (t, 2H), 4.07 (t, 2H)

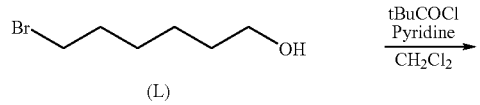

(2) Synthesis of Intermediate (D)

Sodium hydride (an oil content of about 60%, 9.67 g, 242 mmol) and dimethyl sulfoxide (50 mL) were stirred together, and thereto 100 mL of a dimethyl sulfoxide solution containing Compound (A) (38.2 g, 220 mmol, produced by Aldrich Co.) was added dropwise over a 30-minute period. After the resulting mixture was stirred for 30 minutes at room temperature, 100 mL of a dimethyl sulfoxide solution containing Brimide (B) (58.3 g, 220 mmol) was added dropwise thereto. The mixture was reacted for 1 hour at temperatures ranging from 80 to 90° C., the resultant reaction solution was stood to cool, and then the reaction was stopped by addition of water. The organic layer was extracted twice with ethyl acetate, washed with water and saturated brine for once each. The resultant was dried over anhydrous magnesium sulfate, and then concentrated to yield a crude product (C).

Successively thereto, the crude product (C) was dissolved in 200 mL of methylene chloride, and m-chloroperbenzoic acid (45.6 g, 264 mmol) was slowly poured into the resulting solution. The mixture obtained was stirred for 2 hours at room temperature, and then the methylene chloride was mostly evaporated under reduced pressure at room temperature. The thus treated product was purified by silica gel column chromatography (eluate: 1:99 mixture of methanol with methylene chloride) to give 64.2 g of Intermediate (D) as an oily matter (total yield in two steps: 78%).

NMR spectrum of Intermediate (D)

$^1$H-NMR (CDCl$_3$): δ 1.19 (s, 9H), 1.40–1.72 (1,6H), 1.88 (m, 2H), 4.07 (t, two 2 Hs), 6.75 (d, 1H), 7.12 (dd, 1H), 8.08 (d, 1H)

(3) Synthesis of Intermediate (E)

Intermediate (D) (84.7 g, 226 mmol) was dissolved in 200 mL of ethanol using a reaction vessel shielded with aluminum foil, and thereto 150 mL of an aqueous solution containing sodium hydrosulfide n-hydrate (31.7 g, 566 mmol) was added dropwise. The resulting mixture was heated under reflux for one hour, and then stood to cool. Further, ethyl acetate and saturated brine were poured into the reaction solution, and the organic layer was dried over anhydrous magnesium sulfate, concentrated and purified by silica gel column chromatography (eluate: 1:199 mixture of methanol with methylene chloride) to give 51.0 g of Intermediate (E) as white crystals (in a 69% yield).

NMR Spectrum of Intermediate (E)

$^1$H-NMR (CDCl$_3$): δ 1.20 (s, 9H), 1.40–1.70 (m, 6H), 1.93 (m, 2H), 4.06 (t, two 2 Hs), 6.70 (dd, 1H), 6.74 (d, 1H), 7.82 (d, 1H)

(4) Synthesis of Intermediate (F)

1,6-Hexanediol (M) (200 g, 1.69 mol) was mixed with acetonitrile (400 mL) and triethylamine (236 ml, 1.69 mol) at room temperature, and thereto an acetonitrile solution (400 mL) of tosyl chloride (161 g, 846 nmol) was added dropwise while keeping the solution at a temperature of 10C or below. The reaction solution thus prepared was stirred for 6 hours at room temperature, and then the solvent was distilled away. The reaction mixture obtained was admixed with water, and extracted twice with ethyl acetate. The organic layer was washed with water and saturated brine for once each, then dried over anhydrous magnesium sulfate, and further concentrated. The thus obtained crude product was purified by silica gel column chromatography (eluate: 3:2 mixture of hexane with ethyl acetate) to give 114 g of a monotosylate form of 1,6-hexanediol as an oily matter (in a 52% yield).

The foregoing product (114 g, 441 mmol), methylene chloride (200 mL) and pyridine (37.5 mL, 463 mmol) were mixed together at room temperature, and thereto pivaloyl chloride (54.4 mL, 441 mmol) was added dropwise. The resulting mixture was stirred for 6 hours at room temperature, admixed with water, and then extracted twice with methylene chloride. The organic layer was washed with water and saturated brine for once each, dried over anhydrous magnesium sulfate, and then concentrated. The thus obtained crude product was purified by silica gel column chromatography (eluate: 92:8 mixture of hexane with ethyl acetate) to give 120 g of Intermediate (F) as an oily matter (in a 77% yield).

NMR Spectrum of Intermediate (F)

$^1$H-NMR (CDCl$_3$): δ 1.20 (s, 9H), 1.35 (m, 4H), 2.50–2.70 (m, 4H), 2.45 (s, 3H), 4.01 (t, teo 2 Hs), 7.34 (d, 2H), 7.80 (d, 2H)

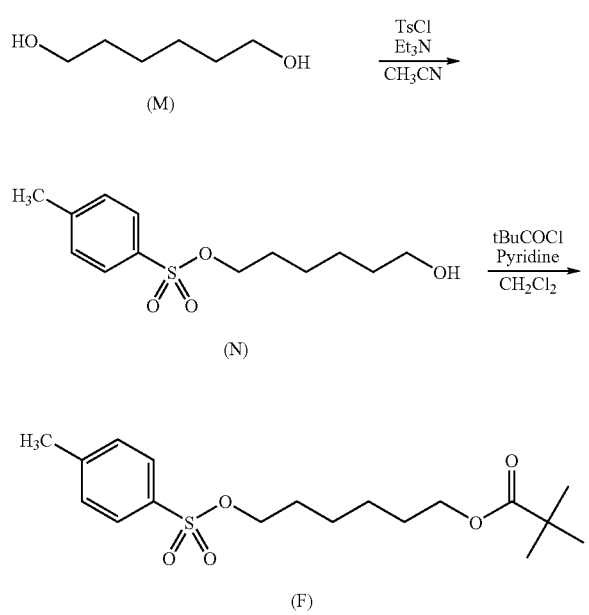

(5) Synthesis of Intermediate (G)

Intermediate (E) (51.0 g, 156 mmol) was dissolved in 200 mL of acetonitrile using a reaction vessel shielded with aluminum foil, and thereto potassium carbonate (64.6 g, 467 mmol), tetrabutylammonium hydrogen sulfate (5.29 g, 15.6 mmol) and tosylate (F) (55.5 g, 156 mmol) were poured sequentially, and stirring was continued for 11 hours at room temperature. The precipitate thus formed was removed by filtration as it was washed with acetonitrile and water, and the filtrate was concentrated and purified by silica gel column chromatography (eluate: 1:99 mixture of methanol with methylene chloride) to give 23.9 g of Intermediate (G) as an oily matter (in a 30% yield).

NMR Spectrum of Intermediate (G)

$^1$H-NMR (CDCl$_3$): δ 1.20 (s, two 9 Hs), 1.40–1.70 (m, 12H), 1.85 (m, 2H), 1.95 (m, 2H), 4.00 (t, 2H), 4.07 (t, two 2 Hs), 4.42 (t, 2H), 6.52 (dd, 1H), 6.60 (d, 1H), 7.49 (d, 1H)

(6) Synthesis of Exemplified Compound (I-1)

Intermediate (G) (23.9 g, 46.7 mmol) was dissolved in 200 mL of methanol in a reaction vessel shielded with aluminum foil, and thereto potassium carbonate (51.6 g, 374 mmol) was added. The resulting mixture was stirred for 4.5 hours at 50° C. After the reaction solution was stood to cool, the precipitate thus formed was removed by filtration, and the filtrate was concentrated and purified by silica gel column chromatography (eluate: methanol-methylene chloride mixtures varying in mixing ratio from 2:98 to 1:9) to give 8.02 g of the exemplified compound (I-1) as an oily matter (in a 50% yield).

NMR Spectrum of Exemplified Compound (I-1)

$^1$H-NMR (CDCl$_3$): δ 1.40–1.70 (m, 12H), 1.85 (m, 2H), 1.95 (m, 2H), 3.67 (t, two 2 Hs), 4.01 (t, 2H), 4.42 (t, 2H), 6.53 (dd, 1H), 6.61 (d, 1H), 7.51 (d, 1H)

<Measurement of Photo-Decomposability>

The exemplified compound (I-1) synthesized in the foregoing process was dissolved into ethyl acetate so that it had a concentration of $5.0 \times 10^{-5}$ mol/L, and poured in a 1-cm quartz cell. The absorbance thereof was measured with an absorption photometer (Multichannel Detector PMA 11, trade name, manufactured by Hamamatsu Photonics K.K.). The absorbance of this solution at 370 nm was found to be 0.64. After this solution was exposed for 20 seconds by means of a fluorescent lamp of 23 watts having the central wavelength of light emission at 365 nm, which was placed at a distance of 45 mm, the absorbance thereof was measured in the same manner as the above. As a result, it was found that the absorbance at 370 nm was lowered to 0.15. Since the materials produced by the decomposition had no absorption in the vicinity of 370 nm, these measurement results prove that the pyrithione compound represented by formula (I) according to the present invention is photo-decomposable.

Example 2

<Synthesis of Exemplified Compound (I-2)>

The exemplified compound (I-2) was synthesized (in oily form) in the same manner as the exemplified compound (I-1), except that 4-bromobutyl pivalate was used in place of Intermediate (B) and 4-tosyloxybutyl pivalate was used in place of Intermediate (F).

NMR Spectrum of Exemplified Compound (I-2)

$^1$H-NMR (DMSO-d$_6$): δ 1.60–1.90 (m, 8H), 3.48 (m, 4H), 3.97 (t, 2H), 4.32 (t, 2H), 4.48 (m, 2H, hydroxyl group), 6.73 (dd, 1H), 6.94 (d, 1H), 8.00 (d, 1H)

Example 3

<Synthesis of Exemplified Compound (I-14)>

The exemplified compound (I-14) was synthesized in accordance with the following scheme:

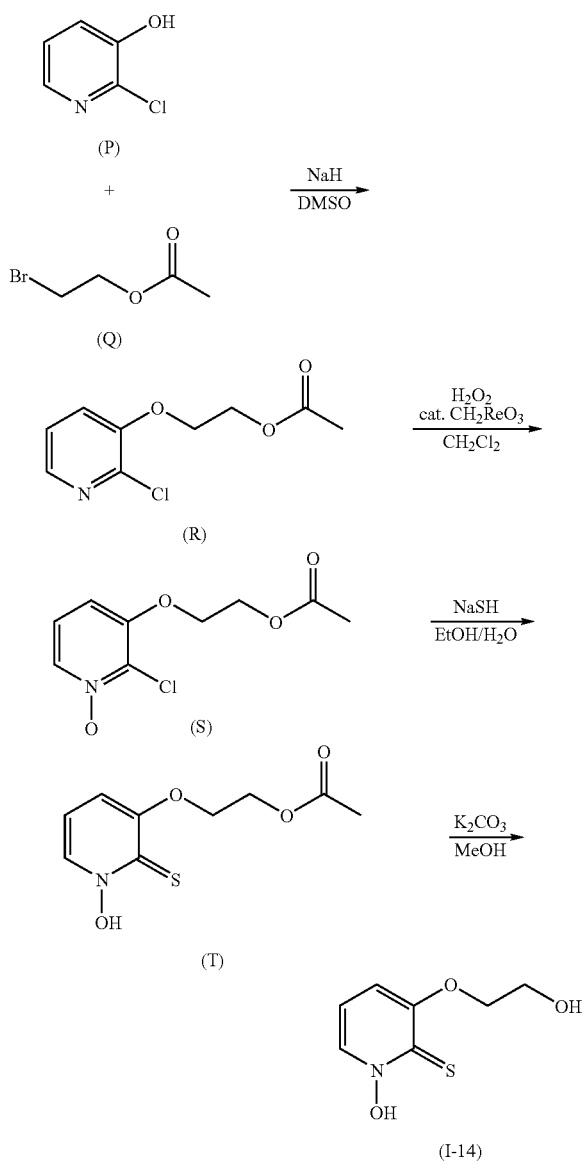

(1) Synthesis of Intermediate (R)

2-Chloro-3-hydroxypyridine (P) (51.4 g, 397 mmol, produced by Aldrich Co.) and dimethyl sulfoxide (200 mL) were mixed together. Into this mixture, which was cooled in an ice bath, sodium hydride (an oil content of about 60%, 19.1 g, 476 mmol) was poured as it was well washed with dimethyl sulfoxide (100 mL). Further thereto, 2-bromoethyl acetate (Q) (66.3 g, 397 mmol) prepared in advance by acetylation of 2-bromoethanol in an ordinary manner was added dropwise. After 2 hours' stirring was performed at 50° C., the resulting reaction mixture was admixed with water, and extracted twice with ethyl acetate. The resultant organic layer was washed with water and saturated brine for once each, dried over anhydrous magnesium sulfate, and then concentrated. The thus obtained crude product was purified by silica gel column chromatography (eluate: 7:3 mixture of hexane with ethyl acetate) to give 69.9 g of Intermediate (R) as an oily matter (in an 82% yield).

NMR Spectrum of Intermediate (R)

$^1$H-NMR (CDCl$_3$): δ 2.11 (s, 3H), 4.27 (t, 2H), 4.50 (t, 2H), 7.22 (m, 2H), 8.03 (dd, 1H).

(2) Synthesis of Intermediate (S)

Intermediate (R) (69.2 g, 321 mmol) was mixed with methylene chloride (230 mL), and cooled in an ice bath. Thereto, methyltrioxorhenium (8.00 g, 32.1 mmol, produced by Aldrich Co.) and 30% aqueous hydrogen peroxide (72.8 g, 642 mmol) were added. After stirring for 15.5 hours at room temperature, the resulting reaction mixture was extracted with methylene chloride, dried over anhydrous magnesium sulfate, and then concentrated. The thus obtained crude product was purified by silica gel column chromatography (eluate: 95:5 mixture of chloroform with ethanol) to give 44.6 g of Intermediate (S) as white crystals (in a 60% yield).

NMR spectrum of Intermediate (S)

$^1$H-NMR (CDCl$_3$): δ 2.13 (s, 3H), 4.31 (t, 2H), 4.50 (t, 2H), 6.86 (dd, 1H)

(3) Synthesis of Intermediate (T)

Intermediate (S) (44.3 g, 191 mmol) was mixed with ethanol (150 mL), and thereto 100 mL of an aqueous solution containing sodium hydrosulfide n-hydrate (21.4 g, 382 mmol) was added dropwise. The resulting mixture was stirred for 4.5 hours at 46–47° C., and then stood to cool, and further rendered acidic (pH=3–4) by use of an aqueous hydrochloric acid. The reaction mixture thus obtained was extracted with methylene chloride, and washed with saturated brine. Thereafter, the resulting organic layer was dried over anhydrous magnesium sulfate, and concentrated. The thus obtained crude product was purified by silica gel column chromatography (eluate: chloroform) to give 28.3 g of Intermediate (T) as white crystals (in a 65% yield).

NMR Spectrum of Intermediate (T)

$^1$H-NMR (CDCl$_3$): δ 2.13 (s, 3H), 4.30 (t, 2H), 4.52 (t, 2H), 6.72 (dd, 1H)

(4) Synthesis of Exemplified Compound (I-14)

Intermediate (T) (10.1 g, 44.0 mmol) was mixed with methanol (120 mL) and cooled in an ice bath, and thereto potassium carbonate (12.2 g, 87.9 mmol) was added. The resulting mixture was stirred for 1 hour at 10° C., and the solid matter formed was removed by filtration. The filtrate was concentrated, and the precipitate thus formed was filtered off as it was washed with methanol, and dried to give 3.20 g of the exemplified compound (I-14) as white crystals (in a 39% yield).

NMR Spectrum of Exemplified Compound (I-14)

$^1$H-NMR (D$_2$O): δ 3.89 (t, 2H), 4.06 (t, 2H), 6.76 (dd, 1H), 6.84 (dd, 1H),

Example 4

<Synthesis of Exemplified Compound (I-3)>

The exemplified compound (I-3) was synthesized (in oily form) in the same manner as the exemplified compound (I-14), except that 3-bromo-2-methylpropyl acetate was used in place of the compound (Q).

NMR Spectrum of Exemplified Compound (I-3)

$^1$H-NMR (DMSO-d$_6$): δ 1.00 (d, 3H), 2.05 (m, 1H), 3.48 (m, 2H), 3.94 (m, 2H), 4.58 (t, 1H), 6.90 (dd, 1H), 7.10 (d, 1H), 8.23 (d, 1H), 12.31 (s, 1H)

Example 5

<Synthesis of Exemplified Compound (I-4)>

The exemplified compound (I-4) was synthesized (in white-crystal form) in the same manner as the exemplified compound (I-14), except that 4-chlorobutyl acetate prepared from 4-chlorobutanol in an ordinary method was used in place of 2-bromoethyl acetate (Q).

NMR Spectrum of Exemplified Compound (I-4)

$^1$H-NMR (CDCl$_3$): δ 1.82 (m, 2H), 2.08 (m, 2H), 3.80 (t, 2H), 4.11 (t, 2H), 6.72 (dd, 1H), 6.78 (dd, 1H), 7.83 (dd, 1H), 12.10 (s, 1H)

Example 6

<Synthesis of Exemplified Compound (I-15)>

The exemplified compound (I-15) was synthesized in accordance with the following scheme:

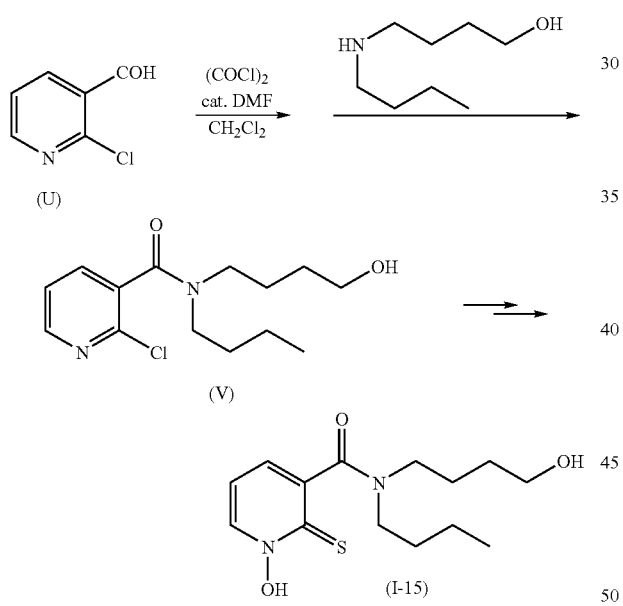

(1) Synthesis of Intermediate (V)

2-Chloronicotinic acid (U) (27.0 g, 171 mmol, produced by Aldrich Co.) was mixed with methylene chloride (150 mL) and cooled in an ice bath, and thereto oxalyl chloride (22.4 mL, 257 mmol) and dimethylformamide were sequentially added dropwise in this order. The resulting mixture was heated under reflux for 2 hours, and then the solvent was distilled away. The residue was admixed with methylene chloride (30 mL) again, and added dropwise to a mixture of 4-(n-butylamino)-1-butanol (24.9 g, 171 mmol), triethylamine (23.9 mL, 171 mmol) and methylene chloride (120 ml) while maintaining the reaction solution temperature at 5° C. or below. Thereafter, the reaction solution was stirred for 1.5 hours at room temperature, admixed with water, and then extracted with methylene chloride. The extract obtained was washed with water and saturated brine for once each, dried over anhydrous magnesium sulfate, and then concentrated. The thus obtained crude product was purified by silica gel column chromatography (eluate: 96:4 mixture of methylene chloride with methanol) to give 29.2 g of Intermediate (V) as an oily matter (in a 60% yield).

NMR Spectrum of Intermediate (V) (1:1 Mixture of Isomers)

$^1$H-NMR (DMSO-d$_6$): δ 0.69(t) and 0.92(t) (3H in total), 1.00–1.70 (m, 8H), 2.80–4.30(t) and 4.42(t) (1H in total), 7.50 (m, 1H), 7.86 (m, 1H), 8.48 (m, 1H)

(2) Synthesis of Exemplified Compound (I-15)

The exemplified compound (I-15) could be synthesized (in white crystal form) from Intermediate (V) in the same manner as in the case of the exemplified compound (I-14).

NMR spectrum of Exemplified Compound (I-15)

$^1$H-NMR (DMSO-d$_6$): δ 0.70(t) and 0.91(t) (3H in total), 1.00–1.70 (m, 8H), 2.90–4.32(t) and 4.41(t) (1H in total), 6.95 (dd, 1H), 7.43 (dd, 1H), 8.51 (dd, 1H), 12.33 (s, 1H)

Example 7

<Preparation of Multifunctional Isocyanate Composition>

A mixture of 1.7 g of the exemplified compound (I-1) synthesized in Example 1, 2.8 g of m-xylylene diisocyanate and 4.5 g of dried acetonitrile was heated to 50° C. under a nitrogen flow, to dissolve the mixture. The thus-obtained solution was admixed with 1 mg of tin di(2-ethylhexanoate), and further stirred at 50° C. for 30 minutes under a nitrogen flow. In this reaction step, vaporization of acetonitrile occurred, so dried acetonitrile was added to the reaction solution in the same amount as the weight of the acetonitrile vaporized. Thus, an acetonitrile solution containing the following Compound (H) as a main component (solids content: 50%) was obtained.

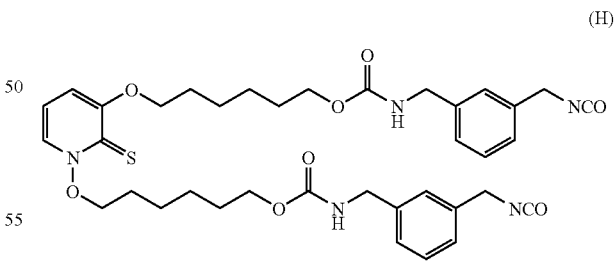

Part of the above-described reaction mixture (acetonitrile solution) was taken out, concentrated under reduced pressure, and then subjected to $^1$H-NMR (DMSO-d$_6$) measurement. In this measurement, the signal derived from the exemplified compound (I-1) (4.5 ppm, hydroxyl groups), which was the starting material, vanished. This measurement result shows that the hydroxyl groups of the exemplified compound (I-1) reacted with the isocyanate compound.

Example 8

<Production of Microcapsule>

(1) Preparation of Phthaloylated Gelatin Solution for Microcapsule Suspension Phthaloylated gelatin (#801 gelatin, trade name, manufactured by Nitta Gelatin Inc.) in an amount of 32 g was mixed with 0.9143 g of 1,2-benzothiazoline-3-one (3.5% methanol solution) and 367.1 g of ion-exchanged water, and heated at 40° C. to prepare an aqueous solution of phthaloylated gelatin.

(2) Preparation of Leuco Dye-encapsulated Micorcapsule Suspension

To 18.1 g of ethyl acetate were added 7.6 g of a leuco dye (Compound (J)) illustrated below, 6.0 g of trimethylolpropane trimethacrylate (LIGHT-ESTER TMP, trade name, manufactured by Kyoeisha Yushi Kagaku Co., Ltd.), 6.0 g of diisopropylnaphthalene (KMC113, trade name, manufactured by Kureha Chemical Industry Co., Ltd.) and 4.0 g of 1,1,3-tris(2-methyl-4-hydroxy-5-t-butylphenyl)butane (ADEKA ARKLS DH-37, trade name, manufactured by ASAHI DENKA CO., LTD.). These ingredients were made into a homogeneous solution by heating. The thus prepared solution was referred to as Mixture-1.

An adduct formed from xylylene diisocyanate and trimethylolpropane (Takenate D110N (75 weight % ethyl acetate solution), trade name, manufactured by Mitsui Takeda Chemicals, Inc.) in an amount of 6.39 g, a phenylisocyanate-formaldehyde condensate (Millionate MR-200, trade name, manufactured by NIPPON POLYURETHANE INDUSTRY CO., LTD.) in an amount of 4.77 g and an adduct formed from xylylene diisocyanate and Compound (K) illustrated below (50% ethyl acetate solution) in an amount of 3.32 g were mixed and homogenized by stirring to prepare a soluiton referred to as Mixture-2. To the Mixture-2 was added 2.5 parts of the wall material solution prepared in Example 7 (the acetonitrile solution containing Compound (H) as a main component (solids content: 50%)), thereby preparing a capsule wall material solution referred to as Mixture-3. Further, the Mixture-1 was mixed with the Mixture-3 to prepare Mixture-4.

Separately, 9.5 g of ion-exchanged water, 0.17 g of Scraph AG-8 (trade name, 50 weight %) manufactured by Nippon Fine Chemical Co., Ltd., 0.43 g of sodium dodecylbenzenesulfonate (10% aqueous solution) and 57.6 g of the phthaloylated gelatin as mentioned above were mixed to prepare Mixture-5.

The Mixture-4 was added to the Mixture-5, and the resulting mixture was emulsified and dispersed at 40° C. by means of a homogenizer (manufactured by Nippon Seiki Co., Ltd.). To the thus obtained emulsion were added 21.2 g of water and 0.12 parts of tetraethylenepentamine. The resulting admixture was homogenized, and underwent encapsulation reaction for 3 hours as it was stirred at 65° C. and the ethyl acetate was removed therefrom. And concentration adjustment was made so that the capsule suspension prepared had a solid concentration of 33%. The diameters of microcapsules in the thus prepared capsule suspension were examined by means of a particle size distribution analyzer (LA-700, trade name, manufactured by HORIBA, LTD.). As a result of the measurement, the median diameter of the microcapsules was found to be 1.10 μm.

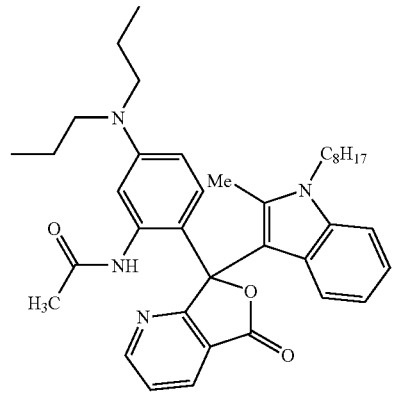

(J)

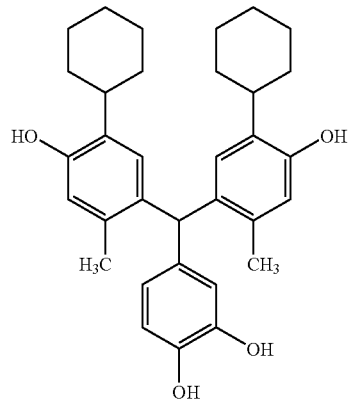

(K)

Me means a methyl group.

<Measurement of Photo-Decomposability>

The leuco dye-encapsulated microcapsule suspension prepared in the foregoing process was coated on a TAC (triacetyl cellulose) support in a coating amount of 7.1 g/m$^2$ on a solid basis. The thus formed coating film was examined for absorbance at 365 nm by means of an absorption photometer (UV3100, trade name, manufactured by Shimadzu Corporation), and its absorbance at 365 mm was found to be 0.8. This coating film was exposed for 20 seconds by means of a fluorescent lamp of 23 watts having the central wavelength of light emission at 365 nm, which was placed at a distance of 8 mm. Thereafter, in the absorbance measurement carried out in the same manner as the above, it was found that the absorbance at 365 nm was lowered to 0.65. This result proves that the microcapsule of the present invention is photo-decomposable.

Having described our invention as related to the present embodiments, it is our intention that the invention not be limited by any of the details of the description, unless otherwise specified, but rather be construed broadly within its spirit and scope as set out in the accompanying claims.

What we claim is:

1. A compound represented by formula (I):

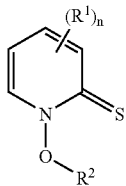

Formula (I)

wherein, in formula (I), R represents -L$^1$-X$^1$ or X$^1$; R$^2$ represents a hydrogen atom or -L$^2$-X$^2$; L$^1$ and L$^2$ each independently represent a divalent linking group selected from the group consisting of an alkylene group, an alkenylene group, an alkynylene group, an arylene group, —O—, —S—, —NR—, —COO—, —NRCO—, —SO$_2$-. and combinations of two or more of these divalent groups, wherein R represents a hydrogen atom or a substituent selected from the group consisting of alkyl group, an aralkyl group, an alkenyl group, an alkynyl group, a hydroxyalkyl group, an aryl group, a carbonyl group, an acyl group, an alkoxycarbonyl group, and an acyloxy group and wherein when L$^1$ or L$^2$ is the combination of an alkylene group and —NR—, R may bond to the alkylene group to form a ring; X$^1$ and X$^2$ each independently represent a group selected from the group consisting a hydroxyl group, an amino group and a mercapto group; n represents an integer of 1 to 4; and when n is 2 or more, R$^1$s may be the same or different.

2. The compound according to claim 1, wherein, in formula (I), n is 1.

3. The compound according to claim 1, wherein, in formula (I), X$_1$ is a hydroxyl group.

4. The compound according to claim 1, wherein, in formula (I), X$^2$ is a hydroxyl group.

* * * * *